(12) United States Patent
Lang et al.

(10) Patent No.: US 7,198,488 B2
(45) Date of Patent: Apr. 3, 2007

(54) DENTAL IMPLANT COMPRISING AN ANCHORING HEAD AND A SCREW ELEMENT

(75) Inventors: Manfred Lang, Altdorf (DE); Jörg Lermer, Nürnberg (DE); Andreas Koch, München (DE)

(73) Assignee: Bredent Dentalgerate Fach- und Organisationsberatung Peter Brehm, Senden (DE)

( * ) Notice: Subject to any disclaimer, the term of this patent is extended or adjusted under 35 U.S.C. 154(b) by 0 days.

(21) Appl. No.: 10/523,736

(22) PCT Filed: Jul. 8, 2003

(86) PCT No.: PCT/EP03/07288

§ 371 (c)(1),
(2), (4) Date: Jan. 16, 2005

(87) PCT Pub. No.: WO2004/012622

PCT Pub. Date: Feb. 12, 2004

(65) Prior Publication Data
US 2005/0250074 A1  Nov. 10, 2005

(30) Foreign Application Priority Data
Jul. 26, 2002 (DE) ................ 102 34 113
Aug. 21, 2002 (DE) ................ 102 38 091

(51) Int. Cl.
*A61C 8/00* (2006.01)
*A61B 17/58* (2006.01)

(52) U.S. Cl. .................... 433/174; 606/73
(58) Field of Classification Search ................ 433/174; 606/73
See application file for complete search history.

(56) References Cited

U.S. PATENT DOCUMENTS

| | | | | |
|---|---|---|---|---|
| 5,456,685 A | * | 10/1995 | Huebner | 606/73 |
| 5,816,812 A | * | 10/1998 | Kownacki et al. | 433/174 |
| 5,871,356 A | * | 2/1999 | Guedj | 433/174 |
| 6,203,324 B1 | * | 3/2001 | Wils | 433/173 |
| 6,565,573 B1 | * | 5/2003 | Ferrante et al. | 606/73 |
| 6,733,291 B1 | * | 5/2004 | Hurson | 433/173 |
| 6,896,517 B1 | * | 5/2005 | Bjorn et al. | 433/174 |

* cited by examiner

*Primary Examiner*—Cary E. O'Connor
(74) *Attorney, Agent, or Firm*—Andrew Wilford

(57) ABSTRACT

A set of dental implants comprising two implants each having an anchoring head for a structural element and having an end face of a predetermined face diameter and a screw element with a thread core and a self-cutting outer thread. The thread core and the outer thread have three segments following one another in succession from crestal to apical, namely a crestal segment adjoining the anchoring head with a constant outer crestal diameter of the outer thread and a thread core conically tapering in the apical direction to a predetermined intermediate diameter, a middle segment with an outer diameter of the thread core substantially equal to the intermediate diameter, and a tip segment with an outer thread of an outer diameter tapering in the apical direction and a conically tapering diameter of the thread core. The face diameters of the two implants are different.

7 Claims, 3 Drawing Sheets

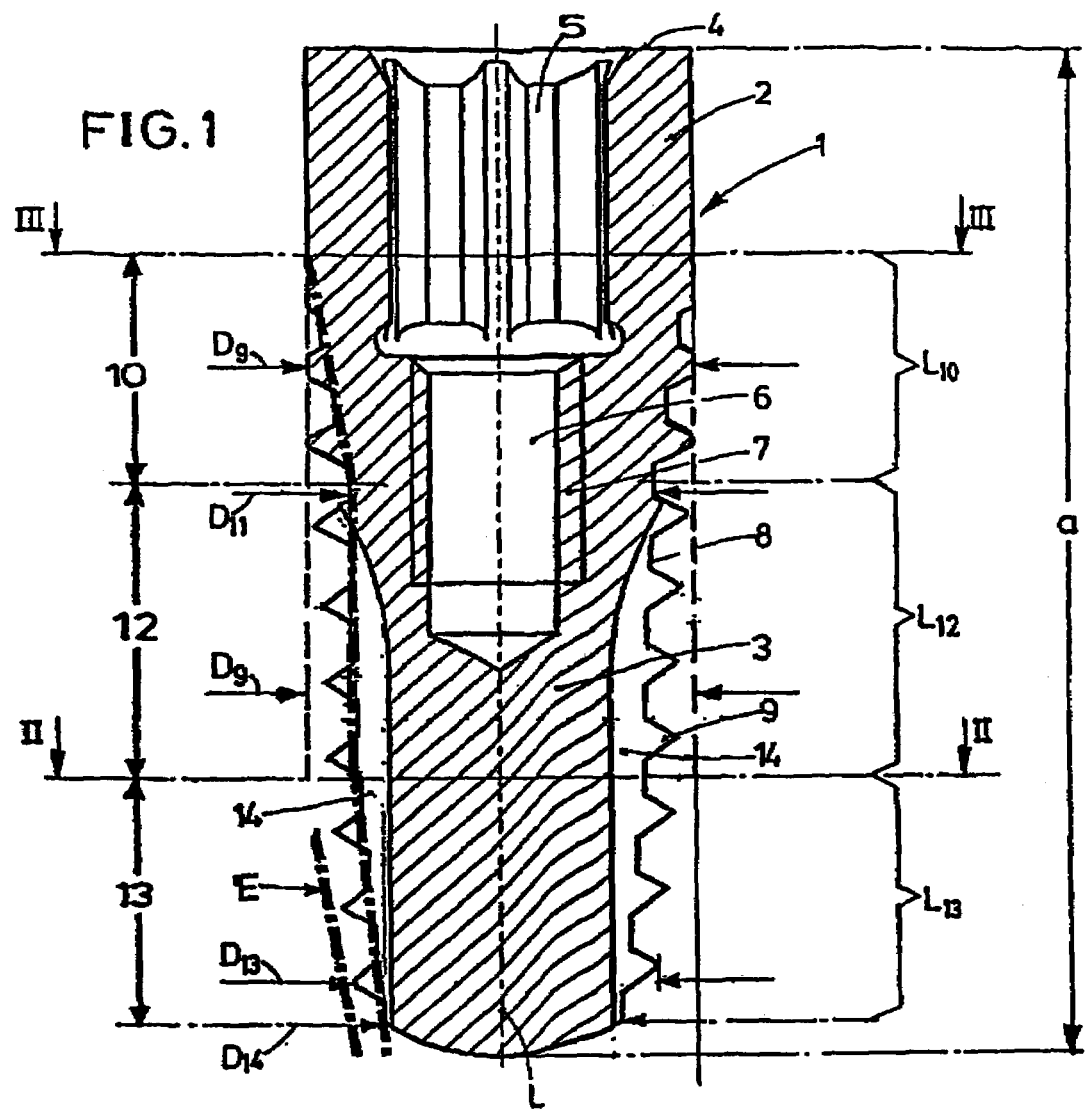
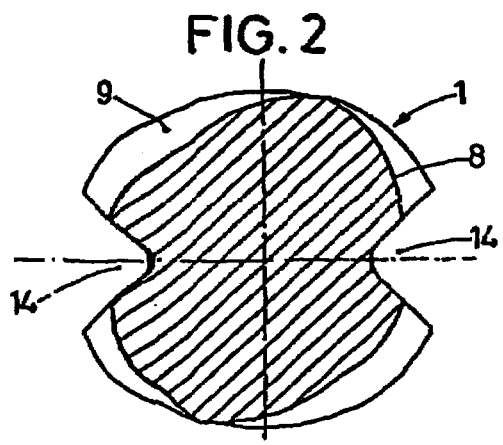
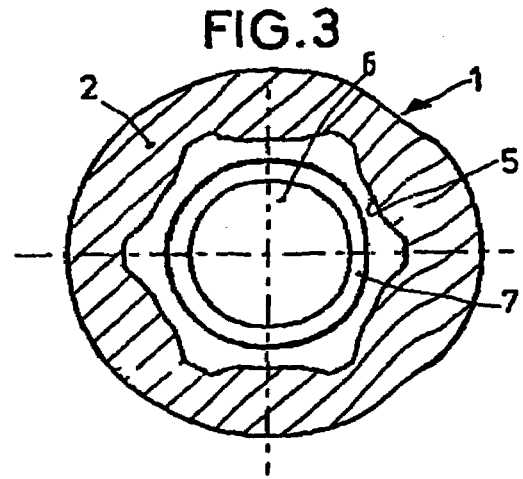

DENTAL IMPLANT COMPRISING AN ANCHORING HEAD AND A SCREW ELEMENT

CROSS REFERENCE TO RELATED APPLICATIONS

This application is the US national phase of PCT application PCT/EP2003/007288, filed 8 Jul. 2003, published 12 Feb. 2004 as WO 2004/012622, and claiming the priority of German patent application 10234113.3 itself filed 26 Jul. 2002 and German patent application 10238091.0 itself filed 21 Aug. 2002.

FIELD OF THE INVENTION

The invention relates to a dental implant with an anchoring head for a structural part and a screw element comprising a threaded core and a self-cutting outer screw thread. The invention also relates to a set of dental implants and to a final drill for creating the finished bore to receive such a dental implant.

BACKGROUND OF THE INVENTION

Screw thread configurations for the screw element of dental implants are known from a number of publications in the state of the art. Thus DE 201 13 254 U1 describes a cylindrical screw implant in which, starting from a cylindrical anchoring head, the screw thread core conically tapered in diameter from crestal to apical while the self-cutting outer screw thread has a constant outer diameter over its length. Because of the fact that the thread becomes increasingly deeper from apical to crestal, at the apical end the implanted screw element forms gaps between the inner wall of the cylindrical final bore in the jaw bone and the thread core which is detrimental on medical grounds.

With the shape of the screw element known from DE 37 35 378 C2, the screw thread has an outer diameter which is constant over the greater part of its length for the thread core and outer thread portion. Only toward the apical end of the screw element does the thread core and outer thread have a slightly conical configuration. Because the greater part of the thread length has a constant outer diameter, this earlier dental implant upon screwing requires relatively greater force with increasing depth to which the implant is screwed into the jaw bone which can result in a relatively strong trauma to the impacted bone tissue.

DE 36 42 901 A1 discloses a special thread for a dental implant which has a relatively strongly conically tapered thread core combined with an outer thread up to a short conical run to the apical end with a constant outer diameter. Here as well the problem arises in that the greatest thread depth is in the region ahead of the apical end.

EP 0 282 789 B1, finally relates to a self-cutting bone implant for dental purposes which can be screwed into the bone and which has a thread configuration which corresponds to that of the first mentioned utility model. To the extent that also combines a conically tapered thread core with an outer thread whose outer diameter is constant, the outer diameter especially is equal to the outer diameter of the cylindrical post anchor.

As further alternatives for the screw element, a screw pattern is claimed in this publication whereby the outer diameter of the outer thread which is equal to the diameter of the cylindrical anchoring head, constantly is reduced toward the free end of the core and a conical thread core is provided. In other words, a conically tapering outer thread is combined with a core which is also conical. As a result of the continuous diameter reduction and the omission of any cylindrical segments in the thread core and/or outer thread, the stability and intrinsic bond between the implant and surrounding bone tissue can be affected.

As can be deduced from the state of the art represented by the publication but not explicit therefrom but known from the actual practice employing dental implants, the bores provided in the jaw bone in all cases have diameters such that the outermost tips of the screw thread rib will penetrate into the bone tissue. The thread turns can be then formed as recesses which grow to stabilize the seat of the implant in the bone tissue. It is desirable to improve such dental implants, especially as to their primary stabilities.

OBJECT OF THE INVENTION

The invention has as its object, starting from the problem of the state of the art to be attacked, to so improve a dental implant with respect to the screw element that the greatest possible stability of the anchoring with the smallest possible stress upon the bone region surrounding the implant can be produced.

SUMMARY OF THE INVENTION

This object is achieved by the instant invention in that the thread core and the outer thread have three segments in succession from the crestal to the apical, namely, a crestal segment connected to the anchoring head with a constant outer diameter of the outer thread and, in the apical direction, a conical thread core, an intermediate segment with basically constant outer diameter of the outer thread with a constant diameter fo the thread core, and a tip segment with a conical outer diameter of the outer thread in the apical direction and constant diameter of the thread core.

Thus cylindrical and conical thread patterns are used both in the thread core and also in the outer thread, to form a combination with optimization of the function of the individual thread segments. In this manner in the apical point segment there is a continuous increase in the cutting cross section and the core diameter to produce a clean cut into the bone of the respective counter thread. The middle segment has practically a cylindrical thread portion without conical or otherwise continuously reducing patterns of the thread core or the outer thread to provide good stability with however a simultaneous balanced loading of the surrounding material by the uniform pressing over its entire area of the screw thread rib. Finally the crestal segment serves to provide a clean transition from the screws body to the anchoring head so that in this region sharp edges and corresponding stress concentration as well as notch effects or sudden changes in the bond tissue are avoided.

This is especially the case when, as in a preferred embodiment is provided, the crestal segment transitions steplessly with its conical thread core into the anchoring head. Upon the implant insertion, the improved thread configuration enables an ideal anchoring in the bone so that an optimal primary stability can be achieved with all bone densities. This primary stability can be enhanced by a subtractive surface area enlargement. By contrast with additive surface area roughening, as is the case with particle coatings, the detrimental shear which is applied by such parts, especially titanium particles, especially with self-cutting threads during insertion, is reduced. Preferably the outer thread of the screw element is configured as a double thread which enables a cleaner insertion of the implant as less bone deterioration. The result is a reduced healing time for the implant.

According to a further preferred embodiment, the ratio of the axial lengths of the crestal or tip [point] segment on the one hand to the middle segment on the other is between about 1:1 to 1:2. Depending upon the respective diameter of the dental implant, with this ratio the anchoring and screw setting characteristics described at the outset can be produced. The same goal is served with a preferred ratio of the thread outer diameter in the crestal and middle segments of the apical end of the point or tip segment of about 4:3.

To anchor the respective structural part [crown] according to a further preferred embodiment of the invention, on the anchoring head there is a hexagonal rounded tooth socket, a so-called Torx® socket which, by contrast to hexagonal straight tooth arrangements of the Allen-type because of their rounded-force engagement surfaces parallel to the screw axis, have a significantly reduced pressure upon the engaged area and thereby less danger of damaging the insertion tool and the structure to be mounted upon the implant. In this manner the implant is able to absorb all of the forces transmitted to it with a high degree of reliability. In addition rounded hexagonal teeth by comparison with planar hexagonal teeth for a given fabrication tolerance can have a significantly better torsional reliability, i.e. security against relative rotation of the interconnected parts.

In addition with a hexagonal socket with its angle of attack of 60° at each individual tooth a greater part of the torque is converted into radial forces which act against the surfaces of the socket and do not participate in the screwing-in force which may be required. The internal hexagonal rounded toothing thus as a whole facilitates the driving of the implant more readily into the bone and provides a corresponding highly stable anchoring against rotation of the structure [crown] which is engaged in the internal teeth.

According to a preferred embodiment of the invention a set of dental implants is provided in which the crestal anchoring surface for the anchoring head and onto which the structure is to be affixed, can have one with a normal outer diameter and two different dental implants with outer diameters which differ. This set configuration is advantageous with such dental implants which may not have the characterizing features of claim 1 as to the thread configuration as well.

As an advantageous set grouping, there can be a three member set having implants in the form of a normal thread implant, a small thread implant and a wide thread implant, whereby in the region of the cylindrical anchoring head all three implant diameters can meet the common normal outer diameter of the anchoring head. This has the significant advantage that one and the same structural components can be used for three different implant diameters without requiring the structural components to be mounted to have stepped diameters, sharp back or front projections or the like between the component to be mounted and the anchoring head. In implant practice, the cost of storage and stocking for the structural components to be affixed to the implant can be reduced corresponding to the number required for a set by the number of implants in the set, here by one-third. With the implant system of the invention by comparison with known implant systems having multiple structural components to be mounted and implants for mounting them, the number can be drastically reduced and significantly limited.

Finally the invention provides a final drill for producing the final bore to receive a dental implant and which has a conical cutting contour with a conical angle matched to the conical pattern of the thread core and an outer diameter matched to the outer diameter of the screw thread. Because of the conical form the dental implant can be set in the jaw such that before the screwing process begins, it will adopt especially well its desired orientation and can then be screwed in substantially especially free from wobbling. In the final screwing into place, the thread rib of the outer thread cuts increasingly into the bone tissue so that the screw thread is initially filled. This achieves a high primary stability.

BRIEF DESCRIPTION OF THE DRAWING

Further features, advantages and details of the invention are given in the following description in which an embodiment is described in greater detail in conjunction with the accompanying drawing. It shows:

FIG. 1 a longitudinal axial section through a dental implant,

FIG. 2 a cross section through the dental implant along section line II—II of FIG. 1, FIG. 3 a section through the dental implant according to section line III—III of FIG. 1, FIG. 4 a side view of the dental implant of FIG. 1 as a normal thread implant, FIG. 5 a side view of a small thread implant, FIG. 6 a side view of a wide thread implant, and FIG. 7 a schematic side view of a final drill.

SPECIFIC DESCRIPTION

Figure 4:
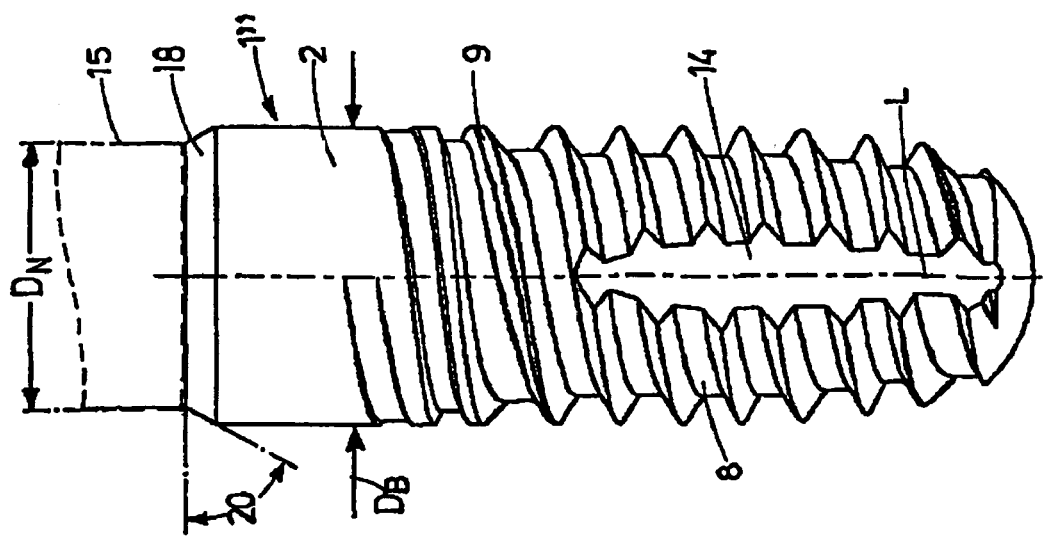
Figure 5:
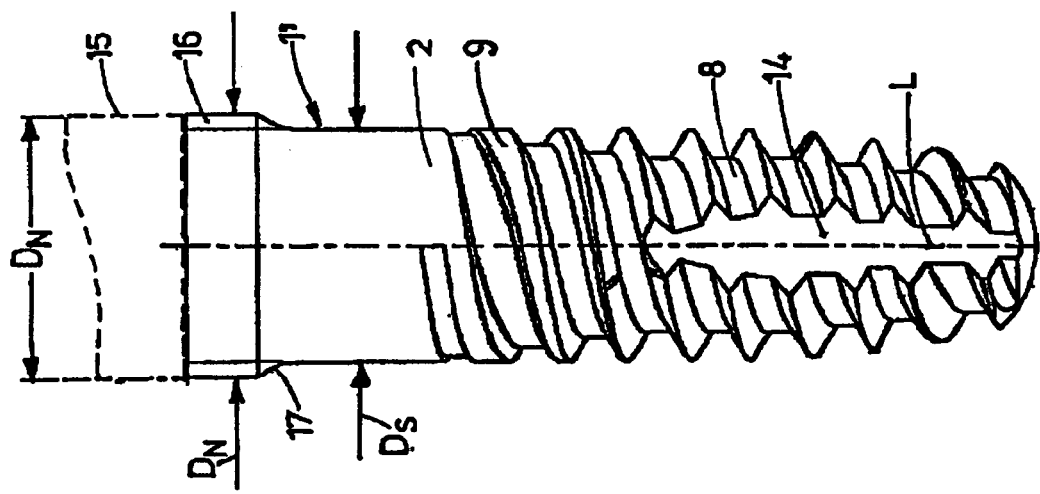
Figure 6:
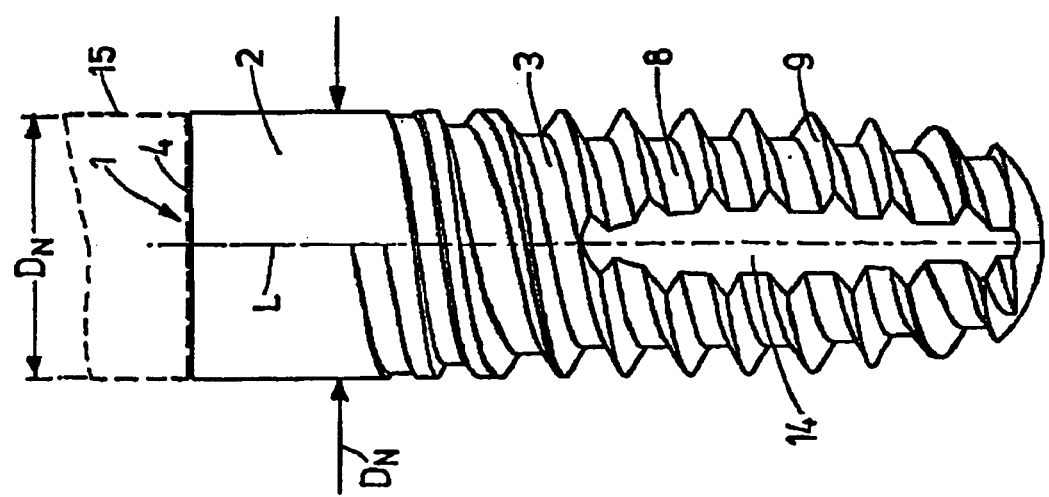

As will be clear from FIGS. 1, 3 and 4, a dental implant 1 has an anchoring head 2 which in its outer contour is rigorously cylindrical and formed in one piece with a screw element 3 extending in an apical direction. The anchoring head 2 has a crestal anchoring area 4 which is coaxial with the longitudinal axis L and is formed with an internal hexagonal set of rounded teeth 5 which serve for engagement in a form fitting manner with an implanting tool or element capable of rotatably driving the implant and for the engagement with the end which can be plugged into the implant of a superstructure 15 or other element to be mounted thereon (FIGS. 4 to 6). The internal teeth 5 terminate in the apical direction at a blind bore 6 with an internal screw thread 7 into which the anchoring screw of the superstructure 15 can be threaded to mount the structure on the implant 1. While the internal teeth 5 extend substantially over the entire length of the anchoring head 2, the blind bore 6 occupies about ⅓; of the length of the screw element 3.

As can be seen especially from FIG. 1, the screw element 3 has a thread core 8 and a self cutting external thread 9. In the direction of the longitudinal axis L, the thread core 8 and the outer thread 9 are subdivided into three segments 10, 12, and 13 following one another from the crestal to the apical, and of which the first crestal segment 10 adjoins the anchoring head 2. In this segment the outer thread 9 has a constant outer diameter $D_9$ of for example 4.5 mm which corresponds to the outer diameter of the anchoring head 2. The thread core 8 runs in this segment 10 conically tapering in the apical direction and diminishes from a diameter corresponding to the diameter $D_9$. The thread core 8 thus merges steplessly into the outer surface of the anchoring head 2. The diameter reduction of the thread core 8 in the segment 10 continues to an intermediate diameter $D_{11}$ which for example is of the order of close to a half millimeter less than the outer diameter $D_9$ of the anchoring head 2.

The middle segment 12 adjoins the crestal segment 10 and in this middle segment 12 the outer diameter $D_{12}$ of the outer thread 9 and the outer diameter $D_{11}$ of the core 8 remain constant. The apparent reduction of the outer diameter in the middle segment is a result of the longitudinal grooves 14 shown in the section of FIG. 1 and described further below.

In the third point or tip segment 13 both the outer thread 9 and the thread core 8 conically taper in the apical direction to a diameter $D_{13}$ or $D_{14}$, respectively. The thread outer diameter $D_{13}$ amounts there, for example, to about 3.5 mm.

To make the above-described thread configuration more clear, the course of the thread core 8 has been illustrated on one side of the section of FIG. 1 in bold dot dash lines. On the same side, also indicated in dot dash lines, is the envelope E of the outer thread 9 at the point or tip segment 13.

As also will be apparent from FIGS. 1 and 2, beginning at the middle segment 12 on two diametrically opposite sides of the screw element 3, two parallel longitudinal grooves 14 are provided which run parallel to the longitudinal axis and have lengths which amount to about ⅔ of the implant length a.

As to the dimensioning of the lengths and diameters of the implant, in addition to the length a=12 mm, the length $L_{10}$ of the crestal segment 10 can amount to 2.8 mm, the length $L_{12}$ of the middle segment 12 can amount to about 3 mm and the length $L_{13}$ of the tip segment 13 can amount to about 3.5 mm. In the case of an implant of total length a=8 mm, the lengths $L_{10}$ and $L_{13}$ of the crestal segment 10 and the tip segment 13 can be only 1.8 mm. The crestal segment 10 and the tip segment 13 are thus each only about half as long as the middle segment 12.

The outer thread 9 itself has a pitch of 1.8 mm and is provided in the tip segment 13 with a chamfer.

FIGS. 4 to 6 show a set of dental implants 1 (FIG. 4), 1' (FIG. 5) and 1" (FIG. 6) whose thread configuration corresponds to that which has been described above. To that extent, no further clarification is required for the dental implants 1' and 1". The dental implant 1 is the normal thread implant 1 of the set in which the anchoring head 2 has a rigorously outer configuration with a normal outer diameter $D_N$ (corresponding to $D_9$). The anchoring area 4 correspondingly has this normal outer diameter $D_N$. The structural part or crown 15 mounted on this head 2, which is held in the internal tooth structure 5 against rotation and is secured by a screw not shown traversing the part 15 and threaded into the internal screw thread 7 has been indicated by broken lines in FIGS. 4 to 6 and has the same normal external diameter $D_N$. Thus between the part 15 and the anchoring head 2, there is a completely flush or smooth transition.

The small thread implant 1' shown in FIG. 5 has an outer diameter $D_S$ corresponding to the outer diameter of the outer thread 9 and the anchoring head 2 and which is smaller than the normal outer diameter $D_N$, in the example about 0.5 mm. For this purpose, the anchoring area 4 again has a diameter corresponding to the normal diameter $D_N$ while the anchoring head 2 has a crestal edge forming a circumferentially wider rib like shoulder 16 whose outer diameter corresponds to the normal diameter $D_N$. The step between the anchoring head 2 and the widening shoulder 16 is provided with an inner radius 17 formed by coining or embossing so that no sharp undercut will be formed on the dental implant 1.

In FIG. 6, a wide thread implant 1" has been illustrated in which the outer diameter $D_B$ of the outer thread 9 at the crestal segment 10 and thus the anchoring head 2 is, for example, 0.5 mm greater than the normal outer diameter $D_N$. Here as well, a matching of the diameter of the anchoring surface 4 to the part 15 to be mounted thereon is required and for this purpose, the anchoring head 2 at its crestal edge a circumferential bevel 18 which delimits the crestal edge 19 of the normal outer diameter $D_N$. The bevel 18 forms a bevel angle 20 with the radial plane of 60° so that here as well, a relatively smooth transition to the mounted part 15 is obtained.

Figure 7:
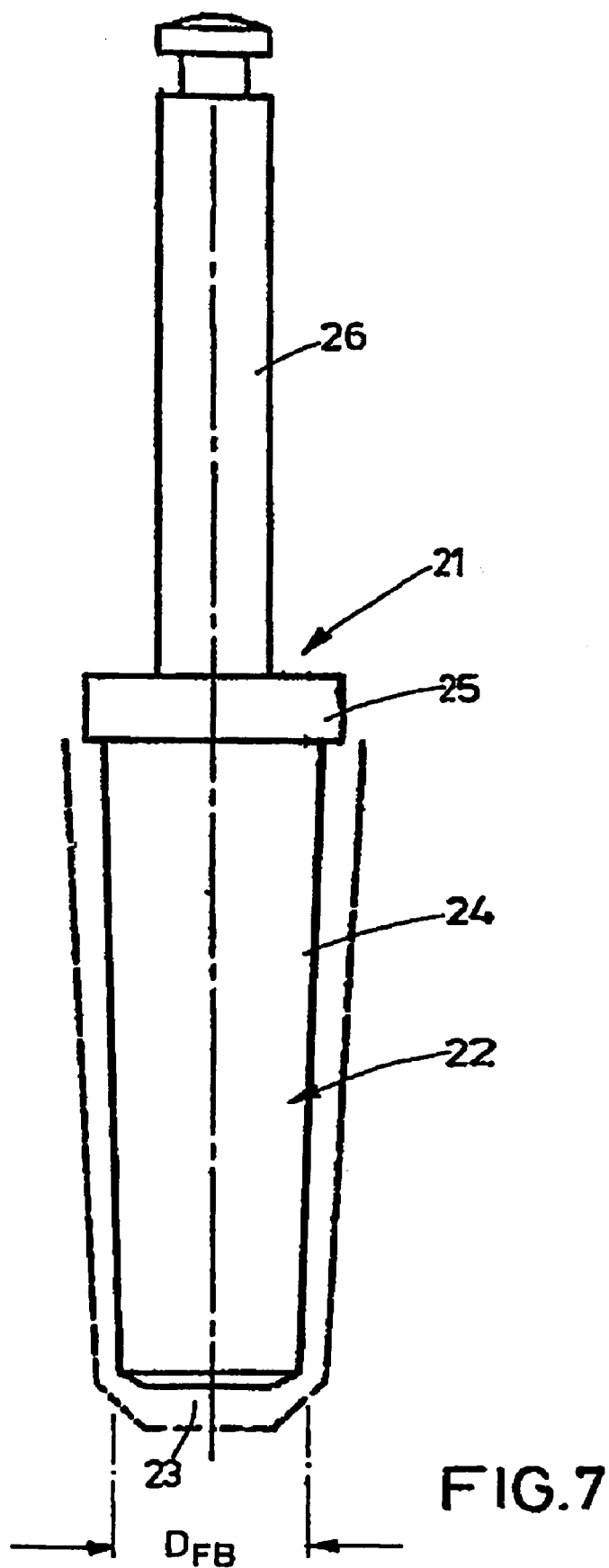

A final drill 21 which serves to form a final bore to accommodate the dental implant 1 illustrated in FIGS. 1 to 4, has been shown in FIG. 7. This final drill 21 has a conical cutting body 22 defining its outer contour and formed by 3 cutters not shown in greater detail. The latter extends from the tip 23 over the surface 24 of the drill 1 to a depth abutment [stop] 25 in the form of a circumferential shoulder. This projects radially both the cutting body 22 and thus limits the drilling depth. The pitch of the cutters not shown usually amounts to, for example, 50 mm so that the active cutting surface of the cutting body reaches from the tip 23 to the abutment 25. This active coating surface has been indicated in FIG. 7 by the broken lines around the cutting body 22. The cutting body 22 tapers toward the tip 23 uniformly and thus has a conical cutting contour whose cone angle is matched to the conical pattern of the cone 8 of the thread of the dental implant 1, that is the conical angle of the crestal segment 10 and the tip segment 13 correspondingly, the outer diameter $D_{FB}$ is matched to the respective outer diameter $D_{11}$, $D_{14}$, that is it varies within several tenths of a mm in the same magnitude.

On the opposite side of the depth abutment from the cutting body 22, the final drill 21 has an anchoring shaft 26 with which the drill 21 can be inserted into a corresponding hand-guided drive head for dental tools.

The invention claimed is:

1. A set of dental implants comprising two implants each comprising:
   an anchoring head for a structural element and having an end face of a predetermined face diameter; and
   a screw element with a thread core and a self-cutting outer thread, the thread core and the outer thread having three segments following one another in succession from crestal to apical, namely
   a crestal segment adjoining the anchoring head with a constant outer crestal diameter of the outer thread and a thread core conically tapering in the apical direction to a predetermined intermediate diameter,
   a middle segment with an outer diameter of the thread core substantially equal to the intermediate diameter, and
   a tip segment with an outer thread of an outer diameter tapering in the apical direction and a conically tapering diameter of the thread core,
the outer crestal diameter of one of the two implants being substantially equal to the face diameter and the outer diameter of the other of the two implants being larger or smaller than the outer crestal diameter.

2. The dental implant according to claim 1, characterized in that the outer thread is formed as a double thread.

3. The dental implant according to claim 1, characterized in that the ratio of the axial lengths of the crestal segment or the tip segment on the one hand to the middle segment on the other hand lies between 1:1 and 1:2.

4. The dental implant according to claim 1, characterized in that the ratio of the thread outer diameter in the crestal segment and the middle segment to that of the apical end of the tip segment lies at about 4:3.5.

5. The dental implant according to claim 1 characterized in that the anchoring head has an internal hexagonal rounded surface toothed socket adjacent a blind threaded bore close to the apical side.

6. A final drill for creating a final bore for a dental implant according to claim 1, characterized in that the final drill has a conical cutting contour with the conical pattern matched to the conical angle of the thread cores and with an outer diameter which corresponds to the outer diameter of the thread cores.

7. A final drill according to claim 6 characterized in that the drill has multiple cutters, preferably three cutters, whereby the cutters extend from the tip over the area of the drill up to a depth stop on the shank.

* * * * *